United States Patent
Michishita et al.

(10) Patent No.: US 6,902,654 B2
(45) Date of Patent: Jun. 7, 2005

(54) ULTRAVIOLET IRRADIATION APPARATUS FOR PHOTOCHEMICAL REACTION AND PREPARATION PROCESS OF VITAMIN D DERIVATIVE MAKING USE OF THE SAME

(75) Inventors: Tadao Michishita, Tokyo (JP); Satoshi Watanabe, Tokyo (JP); Masahiro Katoh, Tokyo (JP); Tetsuhiro Mikami, Tokyo (JP); Kaname Tsuzaki, Tokyo (JP); Koji Oikawa, Tokyo (JP); Makoto Uehara, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/727,507

(22) Filed: Dec. 5, 2003

(65) Prior Publication Data

US 2004/0108198 A1 Jun. 10, 2004

Related U.S. Application Data

(62) Division of application No. 09/720,806, filed as application No. PCT/JP99/03489 on Jun. 29, 1999, now abandoned.

(30) Foreign Application Priority Data

Jul. 3, 1998 (JP) .......................... 10-188879
Jul. 3, 1998 (JP) .......................... 10-188880

(51) Int. Cl.⁷ .......................................... C07C 401/00
(52) U.S. Cl. ................................................. 204/157.67
(58) Field of Search ..................................... 204/157.67

(56) References Cited

U.S. PATENT DOCUMENTS

| 3,638,312 A | 2/1972 | Szwarc et al. ............. 32/15 |
| 4,055,769 A | 10/1977 | Sander .................... 250/492 R |
| 4,702,994 A | 10/1987 | Rendulic et al. ............ 430/306 |
| 5,374,405 A | * 12/1994 | Firnberg et al. ........ 422/186.3 |
| 5,516,970 A | 5/1996 | Miller et al. ................ 588/202 |
| 5,748,288 A | * 5/1998 | Nagano et al. ................ 355/53 |
| 5,906,429 A | * 5/1999 | Mori et al. .................. 362/293 |

FOREIGN PATENT DOCUMENTS

| CH | 249864 | 7/1947 |
| DE | 855397 | 1/1953 |
| DE | 40 14 363 | 11/1991 |
| EP | 0967202 | 12/1999 |
| JP | 49-14541 | 2/1974 |
| JP | 61-176227 | 11/1986 |
| JP | 63-58203 | 4/1988 |

(Continued)

OTHER PUBLICATIONS

Sato et al., "Effect of Wavelength on the Formation of 1 alpha–Hydroxyprevitamin D3 in the Ultraviolet Irradiation of Cholesta–5,7–Diene–1 alpha, 3 beta–Diol and the Use of a Filter Solution in the Photochemical Reaction in the Synthesis of 1 alpha–Hydroxyvitamin D3", J. Nutr. Sci. Vitaminol. vol. 26, No. 6, pp. 545–555, no month, 1980.*

(Continued)

*Primary Examiner*—Edna Wong
(74) *Attorney, Agent, or Firm*—Oblon, Spivak, McClelland, Maier & Neustadt, P.C.

(57) ABSTRACT

A process for preparing a vitamin D derivative including providing an ultraviolet irradiation apparatus for photochemical reactions, which has an ultraviolet radiation-emitting lamp, an optical system which receives light from the ultraviolet radiation-emitting lamp and emits ultraviolet rays having a specific wavelength, and a quartz rod which receives the ultraviolet rays having the specific wavelength from the optical system and emits the ultraviolet rays, irradiating a solution of a provitamin D derivative with the ultraviolet rays emitted from the quartz rod to cause a photochemical reaction to the provitamin D derivative solution, thereby forming a previtamin D derivative, and subjecting the previtamin D derivative to a thermal isomerization reaction to prepare the vitamin D derivative.

43 Claims, 6 Drawing Sheets

FOREIGN PATENT DOCUMENTS

| | | |
|---|---|---|
| JP | 2-3695 | 1/1990 |
| JP | 3-60733 | 3/1991 |
| JP | 3-188061 | 8/1991 |
| JP | 3-284346 | 12/1991 |
| JP | 3-288540 | 12/1991 |
| JP | 4-89473 | 3/1992 |
| JP | 4-89474 | 3/1992 |
| JP | 4-89475 | 3/1992 |
| JP | 4-89476 | 3/1992 |
| JP | 6-72994 | 3/1994 |
| JP | 6-80626 | 3/1994 |
| JP | 8-332372 | 12/1996 |
| JP | 10-72432 | 3/1998 |
| WO | WO 99/39132 | 8/1999 |

OTHER PUBLICATIONS

V. Malatesta, et al., J. Am. Chem. Soc., vol. 103, pp. 6781–6783, "Laser Photochemical Production of Vitamin D"; 1981, no month.

Masami Okabe, et al., J. Org. Chem., vol. 60, No. 3, pp. 767–771, "Synthesis of 25–Hydroxycholecalci-fer–16–en–23–ynol: A Potential Antipsoriatic Agent", 1995, no month.

Tadashi Sato, et al., J. Nutr. Sci. Vitaminol., vol. 26, no. 6, pp. 545–555, "Effect of Wavelength on the Formation of 1α–Hydroxyprevitamin D, in the Ultraviolet Irradiation of Cholesta–5, 7–Diene–1α, 3β–Diol and use of a Filter Solution in the Photochemical Reaction in the Synthesis of 1α–Hydroxy–Vitamin $D_3$", 1980, no month.

William G. Dauben, et al., J . . . Am. Chem. Soc., vol. 104, pp. 5780–5781, "Effects of Wavelength on the Photochemistry of Provitamin $D_3$", 1982, no month.

William G. Dauben, et al., J. Am. Chem. Soc., vol. 110, No. 8, pp. 2548–2553, "Triene Photophysics and Photochemistry: Previtamin $D_3$", 1988, no month.

J.A. Keverling Buisman, et al., Journal of Pharmaceutical Sciences, vol. 57, No. 8, pp. 1326–1329, "Evaluation of the Effect of Isomerization on the Chemical and Biological Assay of Vitamin D", Aug. 1968.

* cited by examiner

PRIOR ART

*FIG. 6*

ULTRAVIOLET IRRADIATION APPARATUS FOR PHOTOCHEMICAL REACTION AND PREPARATION PROCESS OF VITAMIN D DERIVATIVE MAKING USE OF THE SAME

CROSS-REFERENCE TO RELATED APPLICATIONS

The present application is a division of U.S. application Ser. No. 09/720,806, filed Jan. 3, 2001, now abandoned, and a National Stage Application of PCT/JP99/03489, filed Jun. 29, 1999, which claims priority to Japanese Application Serial No. 10-188879, filed Jul. 3, 1998, and Japanese Application Serial No. 10-188880, filed Jul. 3, 1998.

TECHNICAL FIELD

The present invention relates to an ultraviolet irradiation apparatus for photochemical reactions, which is suitable for use in irradiating a photo-reactive solution composed of, for example, a solution of an organic compound with ultraviolet rays having a specific wavelength to cause an intended photochemical reaction of the photo-reactive solution.

The present invention also relates to a process for preparing a vitamin D derivative by irradiating a solution of a provitamin D derivative with ultraviolet rays having a specific wavelength by means of the above-described ultraviolet irradiation apparatus, thereby converting the provitamin D derivative into a provitamin D derivative, or further subjecting the previtamin D derivative to a thermal isomerization reaction to prepare vitamin D derivative.

BACKGROUND ART

In recent years, photochemical reactions, in which a solution of an organic compound is irradiated with ultraviolet radiation to cause a chemical reaction of the organic compound solution, thereby forming another compound from the organic compound, have been conducted in a field of chemical syntheses. The syntheses of, for example, 6-nylon, benzene hexachloride and other compounds have been conducted by utilizing photochemical reactions (Reference "Yuki Gosei Kagaku (Synthetic Organic Chemistry)", written by Hirotada Iida, published by Baifukan, pages 278 and 198).

Figure 6:
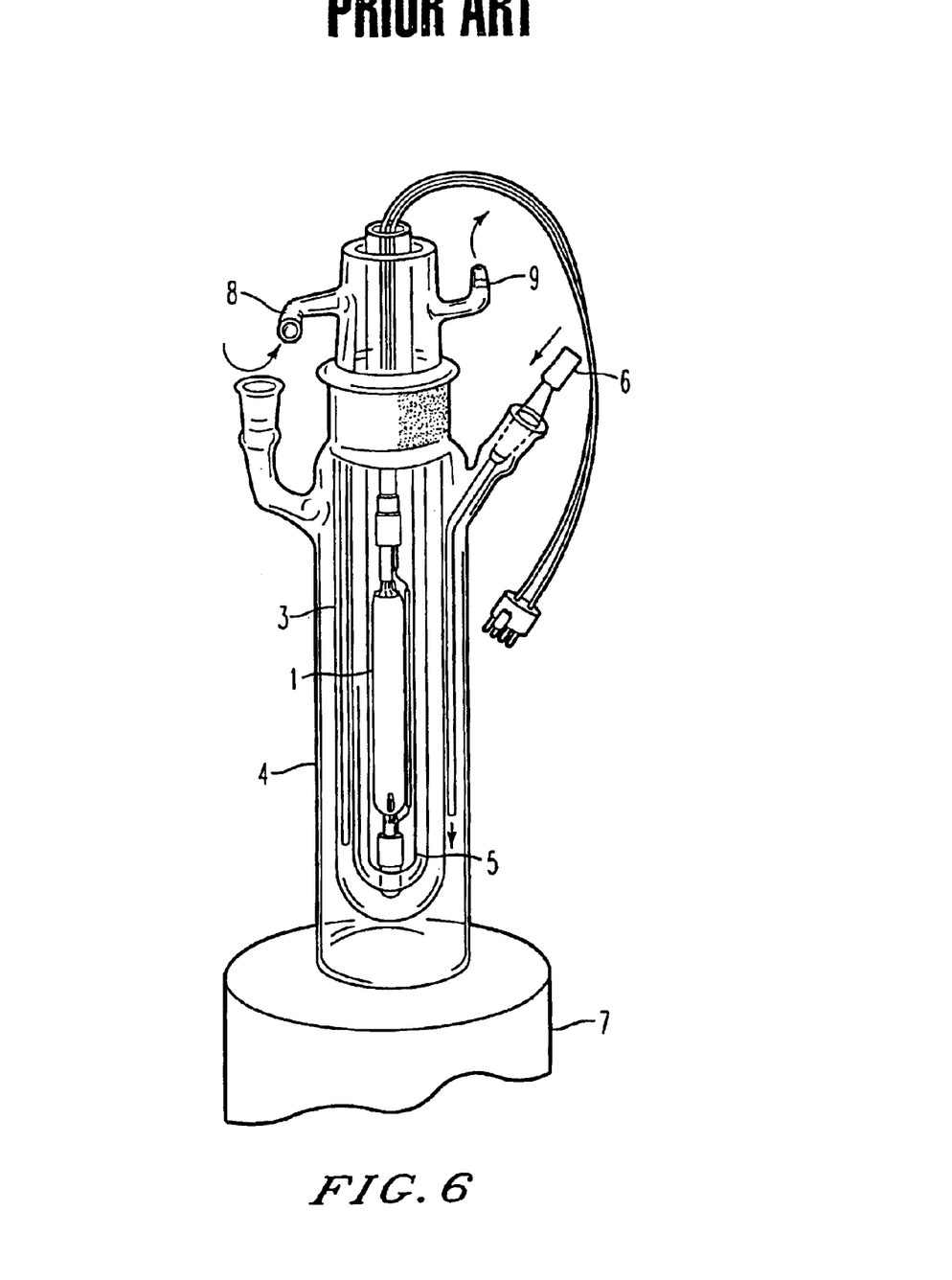
FIG. 6 is an explanatory perspective view illustrating an example of the conventional ultraviolet irradiation apparatus for photochemical reactions.

FIG. 6 is a perspective view illustrating an exemplary ultraviolet irradiation apparatus for such photochemical reactions. In this apparatus, a reaction vessel 4 is made of Pyrex glass, an inner tube 3 is inserted and arranged in this reaction vessel 4 so as to construct a double tube structure together with the reaction vessel 4, a long arc type high pressure mercury lamp 1 is inserted as a light source in the inner tube 3, and a cylindrical Vycor filter 5 is arranged within the inner tube 3 so as to surround the periphery of the high pressure mercury lamp 1.

In this apparatus, a photo-reactive solution is charged into a cylindrical space between the reaction vessel 4 and the inner tube 3 and irradiated with ultraviolet radiation emitted from the high pressure mercury lamp 1 through the Vycor filter 5 in a state that cooling water for cooling the high pressure mercury lamp 1 is running through the inner tube 3 via a cooling water inlet 8 and a cooling water outlet 9 formed at the upper part of the inner tube 3 or in a state that the photo-reactive solution charged into the cylindrical space between the reaction vessel 4 and the inner tube 3 is stirred by, for example, a magnetic stirrer 7 or a stirring rod, or is bubbled with an inert gas such as argon gas introduced through a gas inlet tube 6.

However, the ultraviolet irradiation apparatus of such a construction has involved problems that, since the ultraviolet radiation emitted from the high pressure mercury lamp 1 is struck on the photo-reactive solution through the inner tube 3 necessary for forming a flow path for the cooling water, the intensity of the ultraviolet radiation actually applied to the photo-reactive solution attenuates to become low, and that the ultraviolet radiation emitted from the high pressure mercury lamp 1 is a line spectrum over a wide wavelength range, and so the photo-reactive solution cannot be always irradiated with ultraviolet rays having a wavelength optimum for the intended photochemical reaction at a high efficiency even when the Vycor filter 5 having wavelength selectivity is used.

Here, typical examples of the photochemical reaction include photochemical reactions for synthesizing, for example, vitamin D derivatives. The vitamin D derivatives have been known to be useful as medicines for osteoporosis, hyperparathyroidism, psoriasis, etc.

As a process for synthesizing a vitamin D derivative, there has heretofore been known a process comprising irradiating its corresponding provitamin D derivative with ultraviolet radiation emitted from a high pressure mercury lamp of such an ultraviolet irradiation apparatus as described, for example, above through a Vycor filter or the like and further subjecting the previtamin D derivative obtained by this reaction to a thermal isomerization reaction. However, according to this process, the yield of the intended vitamin D derivative is as low as several percent to ten-odd percent because the yield of the photochemical reaction is low. This fact is as described in, for example, Japanese Patent Application Laid-Open No. 188061/1991, 72994/1994 or 80626/1994.

On the other hand, in order to synthesize a previtamin D derivative, it has also been known to utilize a two-step process of reaction in which a photo-reactive solution is irradiated with a monochromatic laser beam in place of the light from a high pressure mercury lamp having no specificity to obtain a tachysterol derivative as an intermediate product, and the tachysterol derivative is further irradiated with a laser beam having a different wavelength (J. Am. Chem. Soc., Vol. 103, p. 6781 (1981) and Japanese Patent Application Laid-Open Nos. 89473 to 89476/1992).

However, this process is poor in productivity because the efficiency is low due to the use of the laser beams, and hence cannot be practically used on an industrial scale.

In addition, as a two-step process of reaction, it has been reported to cut rays of a wavelength range of 300 to 315 nm among rays emitted from a high pressure mercury lamp by an organic compound typified by a dimethylaminobenzoate, thereby inhibiting the formation of a lumisterol derivative. However, it is necessary to use a photosensitizer for the purpose of converting a tachysterol derivative obtained as an intermediate product into a previtamin D derivative (J. Org. Chem., Vol. 60, p. 767 (1995)). Accordingly, a process for removing it becomes a great problem as a production process of a medical drug.

Besides, it has also been known to use a solution filter upon irradiation of light so as to conduct the irradiation of the light with the wavelength of the light limited. The yield thereof is about 40%, and so a great improvement cannot be expected, and this process also involves a problem from the viewpoint of waste disposal of the compound used as the solution filter (J. Nutr. Sci. Vitamino., Vol. 26, p. 545 (1980)).

On the other hand, in the above-described reaction of the one-step process of light irradiation, the most effective light is known to be ultraviolet rays having a wavelength of 295 nm (J. Am. Chem. Soc., Vol. 104, p. 5780 (1982) and J. Am. Chem. Soc., Vol. 110, p. 2548 (1988)).

Examples of an electric discharge lamp emitting ultraviolet rays within a wavelength range including wavelengths around 295 nm in high intensity, include super high pressure mercury lamps and xenon-mercury lamps. However, since these lamps are short arc type lamps of point light source, their emission length is short, and so such a lamp fails to irradiate the photo-reactive solution sufficiently over the whole region within the reaction vessel 4 with ultraviolet radiation when the lamp is arranged in the interior of the inner tube making up the double tube structure like the apparatus of the construction illustrated in FIG. 6.

When a wavelength-selective filter is used, ultraviolet rays having a required wavelength can be provided. However, an interference filter for selectively taking the ultraviolet rays having the required wavelength out of continuous spectrum light is limited in size to about 100 mm in terms of its diameter for reasons of production. Therefore, such a large-sized filter for covering the whole of an electric discharge lamp such as a super high pressure mercury lamp or xenon-mercury lamp can not be provided.

DISCLOSURE OF THE INVENTION

It is an object of the present invention to provide an ultraviolet irradiation apparatus for photochemical reactions, which is suitable for use in irradiating a photo-reactive solution with ultraviolet radiation to cause a photochemical reaction of the photo-reactive solution and can irradiate the photo-reactive solution with ultraviolet rays having a specific wavelength suitable for the intended photochemical reaction at a high efficiency.

Another object of the present invention is to provide a process by which a provitamin D derivative can be converted into a provitamin D derivative at a high efficiency by means of a photochemical reaction of one-step process of light irradiation, and to provide a process by which a vitamin D derivative can be industrially prepared at a high efficiency utilizing this process.

According to the present invention, there is thus provided an ultraviolet irradiation apparatus for photochemical reactions, which is adapted to irradiate a photo-reactive solution, which undergoes a photochemical reaction by irradiation of ultraviolet radiation, with the ultraviolet radiation, characterized in that the photo-reactive solution is irradiated with ultraviolet rays having a specific wavelength through a quartz rod.

This ultraviolet irradiation apparatus may preferably comprise a condensing and reflecting mirror for condensing and reflecting the ultraviolet radiation, an optical filter which receives the light from the condensing and reflecting mirror and transmits only ultraviolet rays having a specific wavelength, and the quartz rod on which the ultraviolet rays having the specific wavelength from the optical filter are struck.

In the ultraviolet irradiation apparatus, the ultraviolet rays having the specific wavelength from the optical filter may preferably be struck on the quartz rod through a condensing optical system.

According to the present invention, there is also provided an ultraviolet irradiation apparatus for photochemical reactions, which is adapted to irradiate a photo-reactive solution, which undergoes a photochemical reaction by irradiation of ultraviolet radiation, with the ultraviolet radiation, the apparatus comprising an electric discharge lamp which emits light within a wavelength range from an ultraviolet region to an infrared region, a condensing and reflecting mirror for condensing and reflecting the light from the electric discharge lamp, an plane mirror for reflecting the light from the condensing and reflecting mirror, an optical filter on which the light from the plane mirror is struck through an incident lens and which transmits only ultraviolet rays having a specific wavelength, at least one condensing lens on which the ultraviolet rays having the specific wavelength from the optical filter are struck, and a quartz rod on which the ultraviolet rays from the condensing lens are struck, wherein the photo-reactive solution is irradiated with the ultraviolet rays from the quartz rod.

In the above ultraviolet irradiation apparatus, the electric discharge lamp may preferably be a super high pressure mercury lamp or xenon-mercury lamp.

In the ultraviolet irradiation apparatus, at least one of the condensing and reflecting mirror and the plane mirror may preferably have wavelength selective property that light within a wavelength range including ultraviolet rays of the specific wavelength are reflected.

In both ultraviolet irradiation apparatus, the quartz rod may preferably be immersed in the photo-reactive solution within the reaction vessel.

The ultraviolet rays from the quartz rod may be struck on the reaction vessel made of a transparent material, in which the photo-reactive solution is present.

Further, the ultraviolet rays from the quartz rod may be struck on the reaction vessel, in which the photo-reactive solution is present, through a projecting lens.

In the ultraviolet irradiation apparatus, the photo-reactive solution may be a solution of a provitamin D derivative from which a previtamin D derivative is formed by a photochemical reaction, and the ultraviolet rays having the specific wavelength may be ultraviolet rays having a wavelength of 280 to 320 nm.

The process for preparing a vitamin D derivative according to the present invention has been completed by having found that a previtamin D derivative can be formed at a high efficiency by irradiating a solution of a provitamin D derivative with ultraviolet rays having a specific wavelength by means of an ultraviolet irradiation apparatus for photochemical reactions according to the above-described construction, thereby causing a photochemical reaction of the provitamin D derivative solution. According to the present invention, there is thus provided a process for preparing a vitamin D derivative, comprising using an ultraviolet irradiation apparatus for photochemical reactions, which comprises an ultraviolet radiation-emitting lamp, an optical system on which light from the ultraviolet radiation-emitting lamp is struck, and which emits ultraviolet rays having a specific wavelength, and a quartz rod on which the ultraviolet rays having the specific wavelength are struck, irradiating a solution of a provitamin D derivative with the ultraviolet rays having the specific wavelength emitted from the quartz rod of the ultraviolet irradiation apparatus to cause a photochemical reaction to the provitamin D derivative solution, thereby forming a previtamin D derivative, and subjecting the previtamin D derivative to a thermal isomerization reaction to prepare the vitamin D derivative.

In the above process, it may be preferable that the provitamin D derivative is a compound represented by the following general formula 1, the previtamin D derivative is a compound represented by the following general formula 2, and the vitamin D derivative is a compound represented by the following general formula 3.

General Formula 1

General Formula 2

General Formula 3 wherein $R^1$ and $R^3$ individually mean a hydrogen atom or a hydroxyl group which may have a protecting group, $R^2$ denotes a hydrogen atom, a hydroxyl group which may have a protecting group, a lower alkoxy group having 1 to 10 carbon atoms which may be substituted, or a lower alkyl group having 1 to 10 carbon atoms which may be substituted, R is a hydrogen atom or a lower alkyl group having 1 to 10 carbon atoms which may be substituted, and X represents —O—CH$_2$—, —S—CH$_2$—, —CH$_2$—CH$_2$—, —CH=CH— or —N—(R$^4$)—CH$_2$—, in which R$^4$ means a hydrogen atom or a lower alkyl group having 1 to 10 carbon atoms which may be substituted.

According to the present invention, there is also provided a process for preparing a previtamin D derivative, comprising irradiating a solution of a provitamin D derivative represented by the general formula 1 with ultraviolet rays having a specific wavelength emitted from the above-described ultraviolet irradiation apparatus for photochemical reactions to cause a photochemical reaction of the provitamin D derivative solution, thereby forming a previtamin D derivative represented by the general formula 2.

DESCRIPTION OF CHARACTER

1 High pressure mercury lamp
3 Inner tube
4 Reaction vessel
5 Vycor filter
6 Gas inlet tube
7 Magnetic stirrer
8 Inlet for cooling water
9 Outlet for cooling water
11 Electric discharge lamp
12 Elliptical reflecting mirror
13 First plane mirror
14 Incident lens
16 Interference filter
17 Second plane mirror
18 Condensing lens
20 Quartz rod
21 Cap
22 Reaction vessel
L Photo-reactive solution
24 Cooling water jacket
25 Stirrer
27 Gas inlet
28 Gas outlet
29 Magnetic stirrer
30 Tip surface
32 Roughened surface portion
34 Slant portion
40 Projecting lens
44 Cell container
45 Small-sized cell container
46 Solution flow path
48 Solution tank
50 Cooling water circulating mechanism
51 Rotor of magnetic stirrer

BEST MODE FOR CARRYING OUT THE INVENTION

The embodiments of the present invention will hereinafter be described. However, the present invention is not limited to or by these embodiments.

According to the present invention, there is provided an ultraviolet irradiation apparatus for photochemical reactions, which is suitable for use in conducting a photochemical reaction by ultraviolet radiation of a single wavelength or within a narrow wavelength range.

Figure 1:
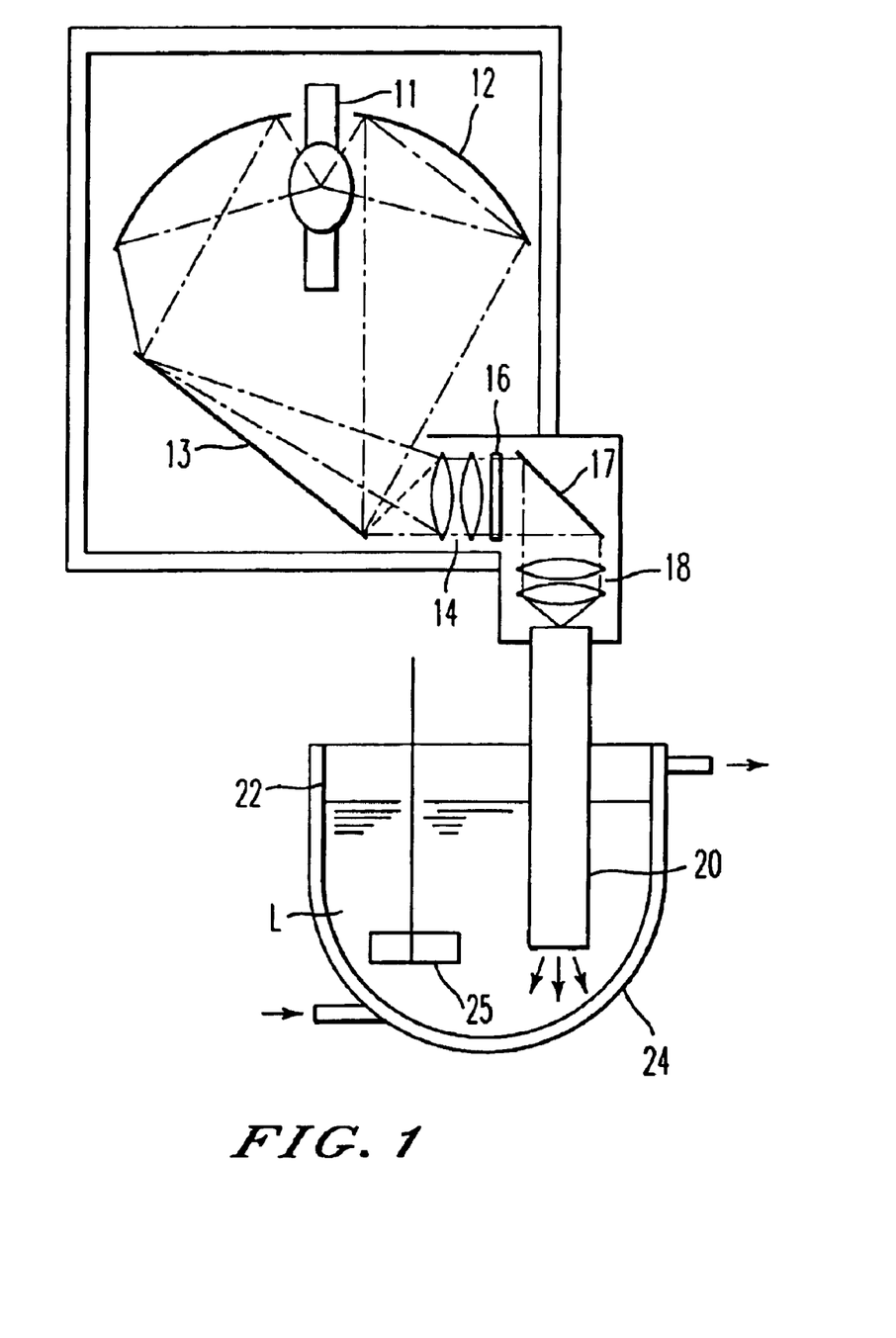
FIG. 1 is an explanatory view illustrating an outline of the whole construction of an ultraviolet irradiation apparatus for photochemical reactions according to an embodiment of the present invention.
Figure 2:
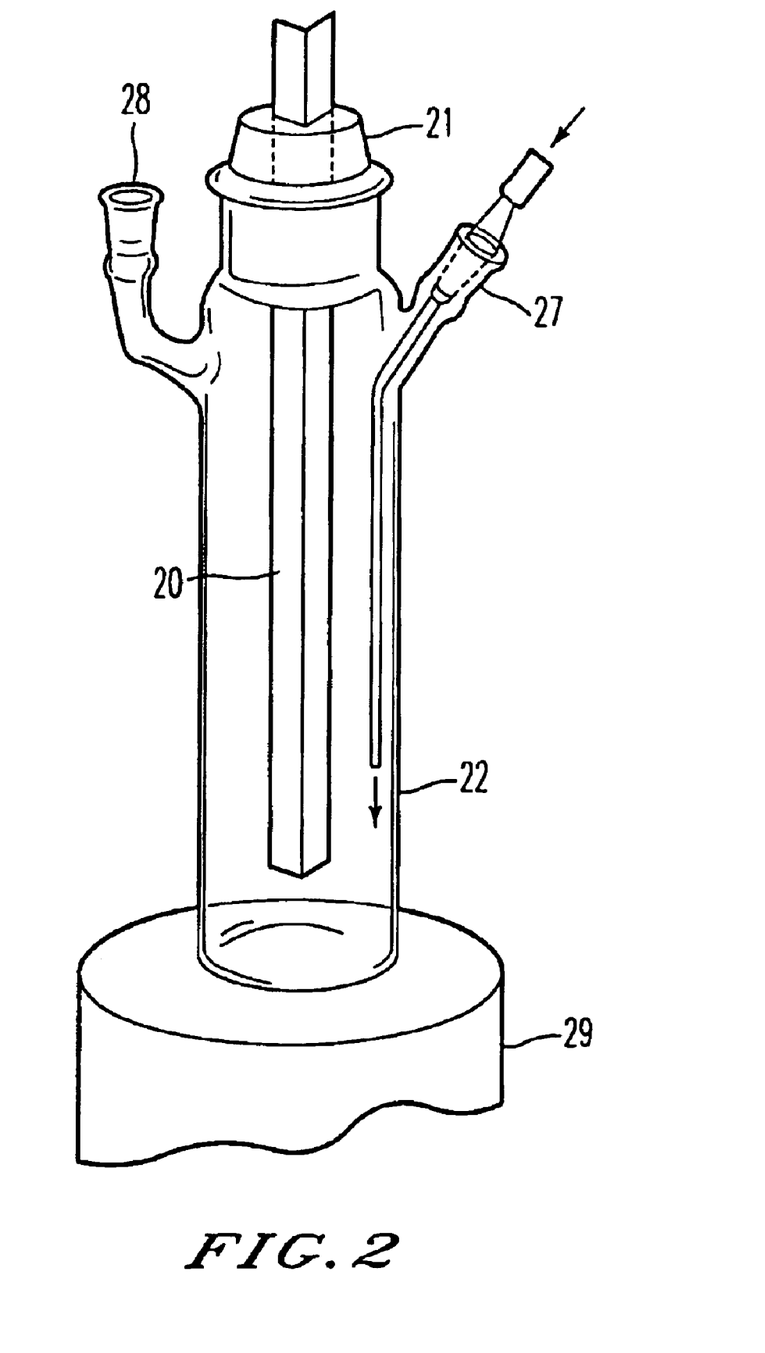
FIG. 2 is a perspective view illustrating an example of the specific construction of a reaction vessel portion in the apparatus shown in FIG. 1.

FIG. 1 is an explanatory view illustrating an outline of the whole construction of an ultraviolet irradiation apparatus for photochemical reactions according to an embodiment of the present invention, and FIG. 2 is a perspective view illustrating an example of the specific construction of a reaction vessel portion in the apparatus shown in FIG. 1.

In FIG. 1, reference numeral 11 indicates an electric discharge lamp that emits ultraviolet radiation, 12 an elliptical reflecting mirror, 13 a first plane mirror, 14 an incident lens, 16 an interference filter, 17 a second plane mirror, 18 a condensing lens, and 20 a quartz rod. In this ultraviolet irradiation apparatus, the elliptical reflecting mirror 12 constitutes a condensing and reflecting mirror, and no limitation is imposed on the condensing and reflecting mirror so far as it has a function that light from the electric discharge lamp 11 is condensed and reflected. However, the elliptical reflecting mirror is particularly preferred.

The electric discharge lamp 11 is composed of a super high pressure mercury lamp or xenon-mercury lamp and arranged in such a manner that the direction of an arc becomes the vertical direction. The light emitted from this electric discharge lamp 11 is condensed by the elliptical reflecting mirror 12 so as to go toward the lower part, reflected by the first plane mirror 13 to go toward the horizontal direction, and struck on the incident lens 14 arranged at a rear position of a focal point and composed of, for example, a plurality of lens elements each of which is a positive lens, namely, the diopter value of which is positive. The light from this incident lens 14 is struck on the interference filter 16 through which only ultraviolet rays having the desired specific wavelength (hereinafter simply referred to as "the ultraviolet rays having the specific wavelength") is selectively transmitted. The ultraviolet rays having the specific wavelength is reflected by the second plane mirror 17 so as to go toward the lower part, and struck on the upper end surface of the quartz rod 20, which is held so as to extend in the vertical direction, through the condensing lens 18 composed of, for example, a plurality of lens elements each of which is a positive lens. In this invention, as the condensing optical system for striking the ultraviolet rays having the specific wavelength from the interference filter 16 on the quartz rod 20, a condensing and reflecting mirror may also be used in place of the condensing lens 18.

In the above, the elliptical reflecting mirror 12 and the first plane mirror 13 are composed respectively of dichroic mirrors, and thereby have wavelength selective property that ultraviolet rays within a specific wavelength range of 254 to 405 nm are reflected, but rays of other far ultraviolet, visible and infrared regions are transmitted. As needed, at least one lens element in the incident lens 14 may be that having wavelength selective property that the ultraviolet rays within the above specific wavelength range are transmitted, but rays within the other wavelength ranges are cut off or attenuated.

The interference filter 16 is composed of an overall dielectric film filter that conducts wavelength selection by wave interference, and the film structure thereof is selected, whereby the filter comes to have property that ultraviolet rays within a narrow wavelength range, for example, ultraviolet rays having a wavelength of 280 to 320 nm, or only ultraviolet rays having a specific wavelength of 295 nm is transmitted at a high efficiency.

The quartz rod 20 is inserted into the interior of the reaction vessel 22 made of a proper material from an upper opening thereof and held therein, whereby at least the tip portion of the quartz rod 20 is in a state immersed in a photo-reactive solution L filled into the reaction vessel 22. Reference numeral 24 indicates a cooling water jacket formed on the outer surface of the reaction vessel 22, and 25 a stirrer.

FIG. 2 illustrates an example of another specific construction of the reaction vessel 22. In this example, the reaction vessel 22 is made of, for example, Pyrex glass, and the quartz rod 20 is inserted into the interior of the reaction vessel 22 from an upper opening thereof and held therein by fitting a cap 21 provided on the midway portion of the quartz rod 20 so as to close the opening of the reaction vessel 22, whereby the quartz rod 20 is held in a state that the tip portion of the quartz rod 20 is positioned close to the bottom of the reaction vessel 22, namely, a state that at least the tip portion of the quartz rod 20 is immersed in a photo-reactive solution filled into the reaction vessel 22. Reference numerals 27 and 28 indicate a gas inlet and a gas outlet, respectively, formed in the reaction vessel 22, and reference numeral 29 designates a magnetic stirrer.

In the above-described construction, not only rays of the ultraviolet region, but also rays of the far ultraviolet, visible and infrared regions are emitted from the electric discharge lamp 11. However, ultraviolet rays within the specific wavelength range of, for example, 254 to 405 nm are provided, by the wavelength selective property of the elliptical reflecting mirror 12 and the first plane mirror 13, and in addition, by the wavelength selective property of the incident lens 14 when it has the wavelength selective property. The ultraviolet rays within this specific wavelength range are transmitted through the interference filter 16, thereby providing ultraviolet rays within a narrower wavelength range of 280 to 320 nm. These ultraviolet rays are struck on the upper end surface of the quartz rod 20 through the second plane mirror 17 and the condensing lens 18.

The ultraviolet rays within this specific wavelength range are transmitted within the quartz rod 20 in a longitudinal direction thereof while repeating total reflection, emitted outside from the lower end portion of the quartz rod 20 and struck on the photo-reactive solution L.

Therefore, in the above-described ultraviolet irradiation apparatus, the transmission loss of the ultraviolet rays having the specific wavelength is low because the ultraviolet radiation transmittance of the quartz rod 20 is high, and moreover the ultraviolet rays having the specific wavelength emitted from the quartz rod 20 are struck on the photo-reactive solution L as it is, since the tip portion of the quartz rod 20 is immersed directly in the photo-reactive solution L. As a result, the intended photochemical reaction of the photo-reactive solution can be caused at an extremely high efficiency. Accordingly, for example, a photochemical reaction, in which a previtamin D derivative is formed from a provitamin D derivative, can be caused at an extremely high efficiency, and after all, a vitamin D derivative can be prepared at a high efficiency.

Figure 3A:
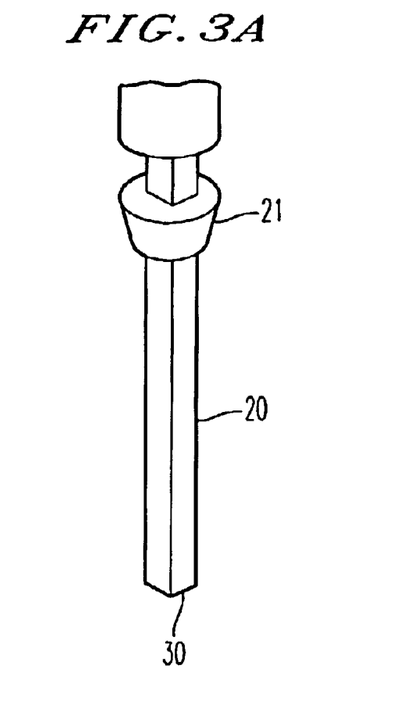
FIGS. 3(A) to 3(C) are explanatory perspective views illustrating examples of a quartz rod used in making up the ultraviolet irradiation apparatus for photochemical reactions.

The ultraviolet rays having the specific wavelength introduced in the quartz rod 20 are generally emitted from the tip surface 30 of the quartz rod 20 when the quartz rod 20 is in the form of a rod having a uniform sectional shape (in the example illustrated, a square pillar shape) as illustrated in FIG. 3(A).

Figure 3B:
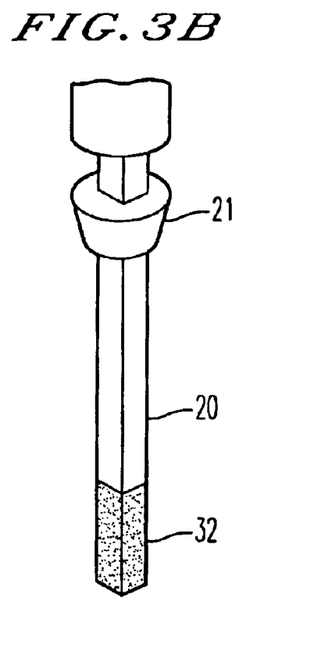

As illustrated in FIG. 3(B), the outer peripheral surface of the tip portion of the quartz rod 20 can be subjected to frosting to form a roughened surface portion 32, thereby providing the roughened surface portion 32 as an ultraviolet emitting surface.

Figure 3C:
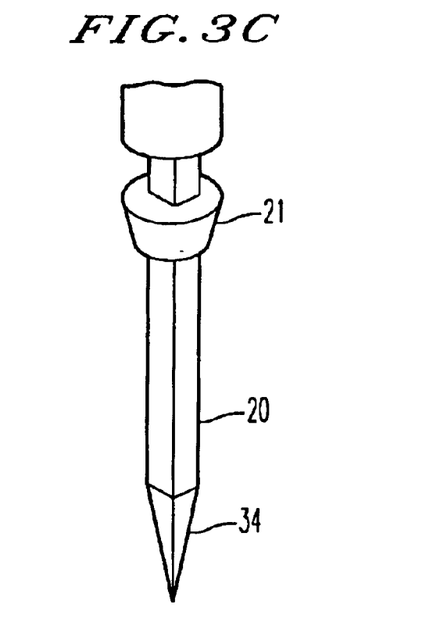

As illustrated in FIG. 3(C), slant portions 34 that come close to the central axis of the quartz rod as they come nearer to the tip thereof are formed at the tip portion of the quartz rod 20, whereby the ultraviolet rays having the specific wavelength may be emitted from the slant portions 34. An angle of the slant portions 34 with the axial direction is preferably at least 30 degrees. It is also effective to subject the slant portions 34 to frosting.

When the quartz rod 20 of such a construction as illustrated in FIG. 3(B) or 3(C) is used, the area of the emitting portion of the ultraviolet rays having the specific wavelength can be increased, and so the intended photochemical reaction can be caused at a still higher efficiency. In addition, the positions or conditions of the roughened surface portion 32 and the slant portions 34 are controlled, whereby the irradiation region of the ultraviolet rays having the specific wavelength and the density of light can be adjusted.

Figure 4:
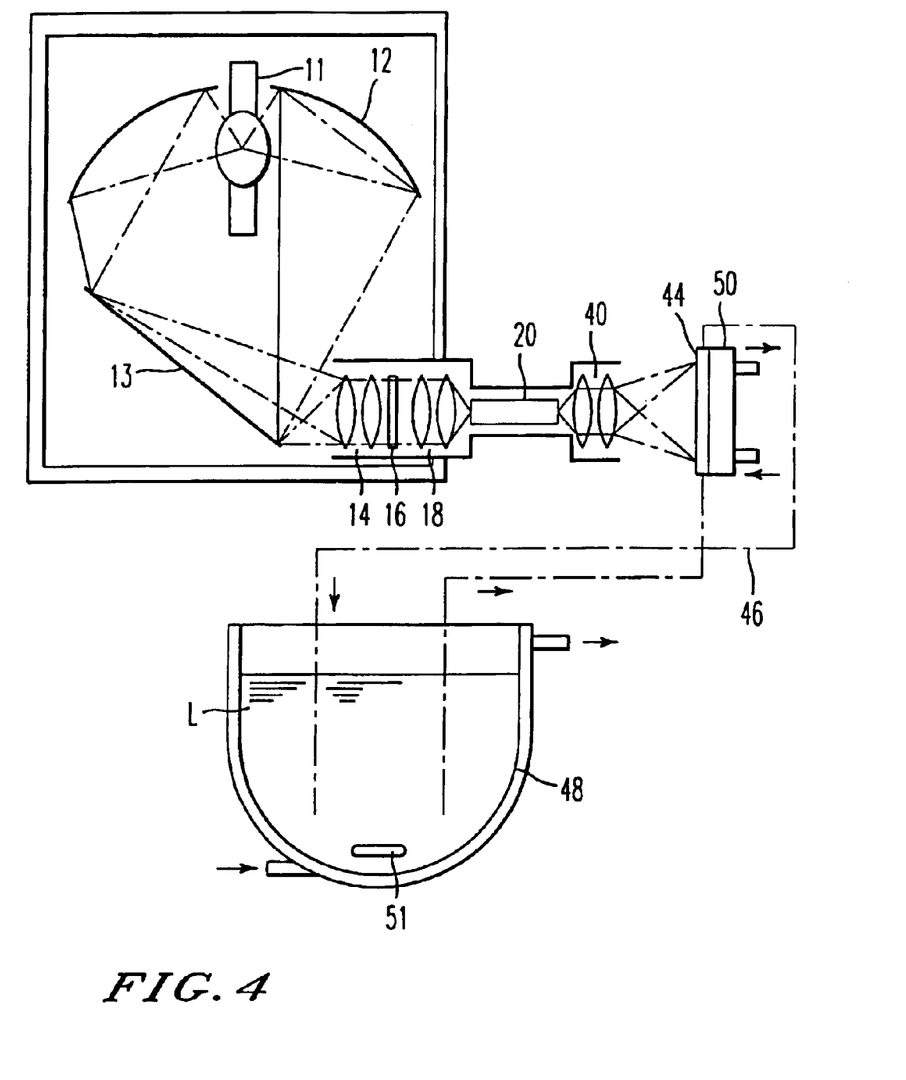
FIG. 4 is an explanatory view illustrating an outline of the construction of an ultraviolet irradiation apparatus for photochemical reactions according to another embodiment.

FIG. 4 is an explanatory view illustrating an outline of the construction of an ultraviolet irradiation apparatus for photochemical reactions according to another embodiment used in the present invention.

In this embodiment, as compared with the apparatus illustrated in FIG. 1, the second plane mirror 17 is removed, and the quartz rod 20 is located so as to extend in the horizontal direction. The ultraviolet rays having the specific wavelength from the condensing lens 18 are struck on one end surface of the quartz rod 20. A projecting lens 40 is arranged on the other end side of the quartz rod 20, and the ultraviolet rays having the specific wavelength emitted from this lens are struck on a cell container 44 made of a transparent material. The cell container 44 forms a solution circulating path together with a solution tank 48, in which the photo-reactive solution L is charged, through a solution flow path 46, and the photo-reactive solution L is caused to pass through the cell container 44 by means of a proper pump (not illustrated). Reference numeral 50 indicates a cooling water circulating mechanism provided on the cell container 44, and 51 a rotor of a magnetic stirrer.

In the apparatus according to this embodiment, the ultraviolet rays having the specific wavelength is guided at a high efficiency by the quartz rod 20, and the loss thereof is low though there is some loss of the ultraviolet rays in that the irradiation of the ultraviolet rays having the specific wavelength is conducted through the wall of the cell container 44. However, the diameter of a spot of the ultraviolet rays having the specific wavelength stuck on the cell container 44 can be controlled to a proper size by the projecting lens 40. Accordingly, the ultraviolet rays having the specific wavelength can be struck at a spot diameter according to the size of the light-receiving surface of the reaction vessel 22, which thus has a merit that the utilization of the ultraviolet rays having the specific wavelength becomes high. In addition, the density of light may also be controlled.

Figure 5:
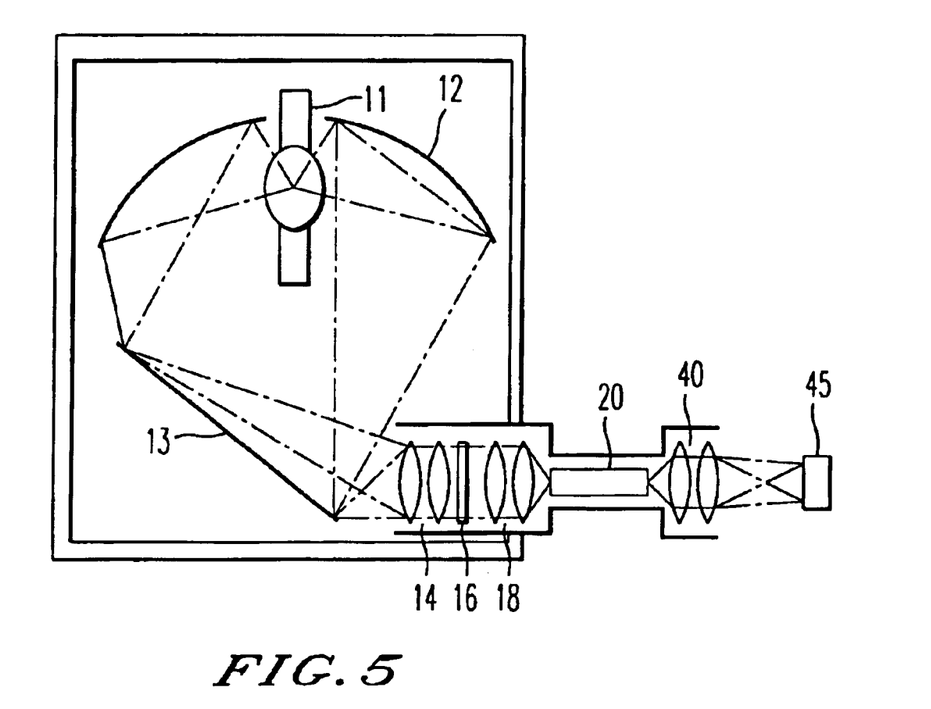
FIG. 5 is an explanatory view illustrating an outline of the construction of a Modified example of the ultraviolet irradiation apparatus for photochemical reactions shown in FIG. 4.

FIG. 5 is an explanatory view illustrating a modified example of the ultraviolet irradiation apparatus for photochemical reactions shown in FIG. 4. In this example, the ultraviolet rays having the specific wavelength from the projecting lens 40 in the apparatus illustrated in FIG. 4 are struck on a small-sized cell container 45 made of a transparent material, in which the photo-reactive solution L is charged. Such a small-sized cell container 45 is advantageously used when the irradiation of the ultraviolet rays is conducted on a relatively small amount of the photo-reactive solution.

In the present invention, the above-described ultraviolet irradiation apparatus is used to irradiate a solution of a provitamin D derivative with ultraviolet rays having a specific wavelength of 280 nm to 320 nm provided from this apparatus, thereby converting the provitamin D derivative into a previtamin D derivative. The previtamin D derivative is further converted into a vitamin D derivative, which is a final intended product, by a thermal isomerization reaction.

The provitamin D derivative is a compound having a skeleton represented by the following formula A, the previtamin D derivative is a compound having a skeleton represented by the following formula B, and the vitamin D derivative is a compound having a skeleton represented by the following formula C.

Formula A

Formula B

Formula C

In the present invention, as specific examples of the provitamin D derivative, previtamin D derivative and vitamin D derivative, are actually preferred those represented by the general formulae 1, 2 and 3, respectively.

In the general formulae 1 to 3, the protecting group of the hydroxyl group, which is represented by $R^1$ or $R^3$ and may have the protecting group, may be any group so far as it functions as a protecting group for the hydroxyl group, and examples thereof include alkyl groups, acyl groups, alkoxycarbonyl groups and silyl groups.

Example of the alkyl groups include linear and branched alkyl groups such as methyl, ethyl, propyl, isopropyl and butyl groups, cycloalkyl groups such as cyclopropyl and cyclobutyl groups, alkoxymethyl groups such as methoxymethyl, methoxyethoxymethyl and benzyloxymethyl groups, and besides a triphenyl methyl group, an ethoxyethyl group and a 2-tetrahydropiranyl group.

Examples of the acyl groups include acetyl, propionyl, butyryl, isobutyryl, benzoyl, methoxyacetyl, triphenylmethoxyacetyl, phenoxyacetyl, chlorodiphenylacetyl, chloroacetyl, trifluoroacetyl and trichloroacetyl groups.

Examples of the alkoxycarbonyl groups include methoxycarbonyl, ethoxycarbonyl, propoxycarbonyl, isopropoxycarbonyl, butoxycarbonyl, phenoxycarbonyl, p-bromophenoxycarbonyl, benzyloxycarbonyl, p-bromobenzyloxycarbonyl, allyloxycarbonyl and dimethylallyloxycarbonyl groups.

Examples of the silyl groups include trimethylsilyl, triethylsilyl, isopropyldimethylsilyl, t-butyldimethylsilyl, t-butyldiphenylsilyl, methyldiisopropylsilyl, tribenzylsilyl and triphenylsilyl groups.

$R^2$ in the general formulae 1 to 3 means a hydrogen atom, a hydroxyl group which may have a protecting group, a lower alkoxy group having 1 to 10 carbon atoms which may be substituted, or a lower alkyl group having 1 to 10 carbon atoms which may be substituted.

Examples of the protecting group of the hydroxyl group which may have the protecting group include the protecting groups mentioned in the description of $R^1$ and $R^3$. Examples of the lower alkoxy group having 1 to 10 carbon atoms which may be substituted include linear and branched alkoxy groups such as methoxy, ethoxy, propoxy, isopropoxy, butoxy, isobutoxy, pentyloxy, hexyloxy, heptyloxy, octyloxy, nonyloxy and decanyloxy groups, cycloalkoxy groups such as cyclopropyloxy and cyclobutyloxy groups, and unsaturated alkoxy groups such as 2-propenyloxy, 2-propynyloxy, 3-butenyloxy and 3-butynyloxy groups. In addition, as hydroxyalkoxy groups, may be mentioned linear and branched hydroxyalkoxy groups such as hydroxymethoxy, hydroxyethoxy, hydroxypropoxy, hydroxyisopropoxy and hydroxybutoxy groups, and cyclic hydroxyalkoxy groups such as hydroxycyclopropyloxy and hydroxycyclobutyloxy group. Examples of the lower alkyl group having 1 to 10 carbon atoms which may be substituted include linear and branched alkyl groups such as methyl, ethyl, propyl, isopropyl, butyl, isobutyl, pentyl, hexyl, heptyl, octyl, nonyl and decanyl groups, cycloalkyl groups such as cyclopropyl and cyclobutyl groups, and unsaturated alkyl groups such as 2-propenyl, 2-propynyl, 3-butenyl and 3-butynyl groups. Geometrical structure of the group having a double bond may be either cis or trans.

X in the general formulae 1 to 3 represents —O—CH$_2$—, —S—CH$_2$—, —CH$_2$—CH$_2$—, —CH=CH— or —N—(R$^4$)—CH$_2$—.

R in the general formulae 1 to 3 means a hydrogen atom or a lower alkyl group having 1 to 10 carbon atoms which may be substituted.

Here, examples of the alkyl group include, in addition of the alkyl groups mentioned above, saturated alkyl groups such as 2-methylpropyl, 1-cyclopropyl-1-hydroxymethyl, 1-hydroxy-1-methylethyl, 2-hydroxy-1-methylethyl, 1,2-dihydroxy-1-methylethyl, 1-ethyl-1-hydroxypropyl, 1-ethyl-2-hydroxypropyl, 1-ethyl-1,2-dihydroxypropyl, 1-hydroxy-1-(n-propyl)butyl, 2-hydroxy-1-(n-propyl)butyl, 1,2-dihydroxy-1-(n-propyl)-butyl, 1-hydroxy-2-methylpropyl, 2-hydroxy-2-methylpropyl, 3-hydroxy-2-methylpropyl, 1,2-dihydroxy-2-methylpropyl, 1,3-dihydroxy-2-methylpropyl, 2,3-dihydroxy-2-methylpropyl, 2-ethyl-1-hydroxybutyl, 2-ethyl-2-hydroxybutyl, 2-ethyl-3-hydroxybutyl, 2-ethyl-1,2-dihydroxybutyl, 2-ethyl-1,3-dihydroxybutyl, 2-ethyl-2,3-dihydroxybutyl, 1-hydroxy-2-(n-propyl)pentyl, 2-hydroxy-2-(n-propyl)pentyl, 3-hydroxy-2-(n-propyl)pentyl, 1,2-dihydroxy-2-(n-propyl)pentyl, 1,3-dihydroxy-2-(n-propyl)pentyl, 2,3-dihydroxy-2-(n-propyl)pentyl, 2-hydroxy-3-methylbutyl, 3-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-ethyl-2-hydroxypentyl, 3-ethyl-3-hydroxypentyl, 3-ethyl-4-hydroxypentyl, 3-ethyl-2,3-dihydroxypentyl, 3-ethyl-2,4-dihydroxypentyl, 3-ethyl-3,4-dihydroxypentyl, 2-hydroxy-3-(n-propyl)hexyl, 3-hydroxy-3-(n-propyl)hexyl, 4-hydroxy-3-(n-propyl)hexyl, 2,3-dihydroxy-3-(n-propyl)hexyl, 2,4-dihydroxy-3-(n-propyl)hexyl, 3,4-dihydroxy-3-(n-propyl)hexyl, 3-hydroxy-4-methylpentyl, 4-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 4-ethyl-3-hydroxyhexyl, 4-ethyl-4-hydroxyhexyl, 4-ethyl-5-hydroxyhexyl, 4-ethyl-3,4-dihydroxyhexyl, 4-ethyl-3,5-dihydroxyhexyl, 4-ethyl-4,5-dihydroxyhexyl, 3-hydroxy-4-(n-propyl)heptyl, 4-hydroxy-4-(n-propyl)heptyl, 5-hydroxy-4-(n-propyl)heptyl, 3,4-dihydroxy-4-(n-propyl)heptyl, 3,5-dihydroxy-4-(n-propyl)heptyl, 4,5-dihydroxy-4-(n-propyl)heptyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-ethyl-4-hydroxyheptyl, 5-ethyl-5-hydroxyheptyl, 5-ethyl-6-hydroxyheptyl, 5-ethyl-4,5-dihydroxyheptyl, 5-ethyl-4,6-dihydroxyheptyl, 5-ethyl-5,6-dihydroxyheptyl, 4-hydroxy-5-(n-propyl)octyl, 5-hydroxy-5-(n-propyl)octyl, 6-hydroxy-5-(n-propyl)octyl, 4,5-dihydroxy-5-(n-propyl)octyl, 4,6-dihydroxy-5-(n-propyl)octyl and 5,6-dihydroxy-5-(n-propyl)octyl groups; and 3-hydroxy-3-methyl-1-butenyl, 4-hydroxy-3-methyl-1-butenyl, 3,4-dihydroxy-3-methyl-1-butenyl, 3-ethyl-3-hydroxy-1-pentenyl, 3-ethyl-4-hydroxy-1-pentenyl, 3-ethyl-3,4-dihydroxy-1-pentenyl, 3-hydroxy-3-(n-propyl)-1-hexenyl, 4-hydroxy-3-(n-propyl)-1-hexenyl, 3,4-dihydroxy-3-(n-propyl)-1-hexenyl, 4-hydroxy-4-methyl-2-pentenyl, 5-hydroxy-4-methyl-2-pentenyl, 4,5-dihydroxy-4-methyl-2-pentenyl, 4-ethyl-4-hydroxy-2-hexenyl, 4-ethyl-5-hydroxy-2-hexenyl, 4-ethyl-4,5-dihydroxy-2-hexenyl, 4-hydroxy-4-(n-propyl)-2-heptenyl, 5-hydroxy-4-(n-propyl)-2-heptenyl, 4,5-dihydroxy-4-(n-propyl)-2-heptenyl, 3-hydroxy-4-methyl-1-pentenyl, 4-hydroxy-4-methyl-1-pentenyl, 5-hydroxy-4-methyl-1-pentenyl, 3,4-dihydroxy-4-methyl-1-pentenyl, 3,5-dihydroxy-4-methyl-1-pentenyl, 4,5-dihydroxy-4-methyl-1-pentenyl, 4-ethyl-3-hydroxy-1-hexenyl, 4-ethyl-4-hydroxy-1-hexenyl, 4-ethyl-5-hydroxy-1-hexenyl, 4-ethyl-3,4-dihydroxy-1-hexenyl, 4-ethyl-3,5-dihydroxy-1-hexenyl, 4-ethyl-4,5-dihydroxy-1-hexenyl, 3-hydroxy-4-(n-propyl)-1-heptenyl, 4-hydroxy-4-(n-propyl)-1-heptenyl, 5-hydroxy-4-(n-propyl)-1-heptenyl, 3,4-dihydroxy-4-(n-propyl)-1-heptenyl, 3,5-dihydroxy-4-(n-propyl)-1-heptenyl, 4,5-dihydroxy-4-(n-propyl)-1-heptenyl, 5-hydroxy-5-methyl-3-hexenyl, 6-hydroxy-5-methyl-3-hexenyl, 5,6-dihydroxy-5-methyl-3-hexenyl, 5-ethyl-5-hydroxy-3-heptenyl, 5-ethyl-6-hydroxy-3-heptenyl, 5-ethyl-5,6-dihydroxy-3-heptenyl, 5-hydroxy-5-(n-propyl)-3-octenyl, 6-hydroxy-5-(n-propyl)-3-octenyl, 5,6-dihydroxy-5-(n-propyl)-3-octenyl, 4-hydroxyl-5-methyl-2-hexenyl, 5-hydroxyl-5-methyl-2-hexenyl, 6-hydroxyl-5-methyl-2-hexenyl, 4,5-dihydroxy-5-methyl-2-hexenyl, 4,6-dihydroxy-5-methyl-2-hexenyl, 5,6-dihydroxy-5-methyl-2-hexenyl, 5-ethyl-4-hydroxy-4-heptenyl, 5-ethyl-5-hydroxy-2-heptenyl, 5-ethyl-6-hydroxy-2-heptenyl, 5-ethyl-4,5-dihydroxy-2-heptenyl, 5-ethyl-4,6-dihydroxy-2-heptenyl, 5-ethyl-5,6-dihydroxy-2-heptenyl, 4-hydroxy-5-(n-propyl)-2-octenyl, 5-hydroxy-5-(n-propyl)-2-octenyl, 6-hydroxy-5-(n-propyl)-2-octenyl, 4,5-dihydroxy-5-(n-propyl)-2-octenyl, 4,6-dihydroxy-5-(n-propyl)-2-octenyl, 5,6-dihydroxy-5-(n-propyl)-2-octenyl, 4-hydroxy-5-methyl-1-hexenyl, 5-hydroxy-5-methyl-1-hexenyl, 6-hydroxy-5-methyl-1-hexenyl, 4,5-dihydroxy-5-methyl-1-hexenyl, 4,6-dihydroxy-5-methyl-1-hexenyl, 5,6-dihydroxy-5-methyl-1-hexenyl, 5-ethyl-4-hydroxy-1-heptenyl, 5-ethyl-5-hydroxy-1-heptenyl, 5-ethyl-6-hydroxy-1-heptenyl, 5-ethyl-4,5-dihydroxy-1-heptenyl, 5-ethyl-4,6-dihydroxy-1-heptenyl, 5-ethyl-5,6-dihydroxy-1-heptenyl, 4-hydroxy-5-(n-propyl)-1-octenyl, 5-hydroxy-5-(n-propyl)-1-octenyl, 6-hydroxy-5-(n-propyl)-1-octenyl, 4,5-dihydroxy-5-(n-propyl)-1-octenyl, 4,6-dihydroxy-5-(n-propyl)-1-octenyl, 5,6-dihydroxy-5-(n-propyl)-1-octenyl, 3-hydroxy-3-methyl-1-butynyl, 4-hydroxy-3-methyl-1-butynyl, 3,4-dihydroxy-3-methyl-1-butynyl, 3-ethyl-3-hydroxy-2-pentynyl, 3-ethyl-4-hydroxy-1-pentynyl, 3-ethyl-3,4-dihydroxy-1-pentynyl, 3-hydroxy-3-(n-propyl)-1-hexynyl, 4-hydroxy-3-(n-propyl)-1-hexynyl, 3,4-dihydroxy-3-(n-propyl)-1-hexynyl, 4-hydroxy-4-methyl-2-pentynyl, 5-hydroxy-4-methyl-2-pentynyl, 4,5-dihydroxy-4-methyl-2-pentynyl, 4-ethyl-4-hydroxy-2-hexynyl, 4-ethyl-5-hydroxy-2-hexynyl, 4-ethyl-4,5-dihydroxy-2-hexynyl, 4-hydroxy-4-(n-propyl)-2-heptynyl, 5-hydroxy-4-(n-propyl)-2-heptynyl, 4,5-dihydroxy-4-(n-propyl)-2-heptynyl, 3-hydroxy-4-methyl-1-pentynyl, 4-hydroxy-4-methyl-1-pentynyl, 5-hydroxy-4-methyl-1-pentynyl, 3,4-dihydroxy-4-methyl-1-pentynyl, 3,5-dihydroxy-4-methyl-1-pentynyl, 4,5-dihydroxy-4-methyl-1-pentynyl, 4-ethyl-3-hydroxy-1-hexynyl, 4-ethyl-4-hydroxy-1-hexynyl, 4-ethyl-5-hydroxy-1-hexynyl, 4-ethyl-3,4-dihydroxy-1-hexynyl, 4-ethyl-3,5-dihydroxy-1-hexynyl, 4-ethyl-4,5-dihydroxy-1-hexynyl, 3-hydroxy-4-(n-propyl)-1-heptynyl, 4-hydroxy-4-(n-propyl)-1-heptynyl, 5-hydroxy-4-(n-propyl)-1-heptynyl, 3,4-dihydroxy-4-(n-propyl)-1-heptynyl, 3,5-dihydroxy-4-(n-propyl)-1-heptynyl, 4,5-dihydroxy-4-(n-propyl)-1-heptynyl, 5-hydroxy-5-methyl-3-hexenyl, 6-hydroxy-5-methyl-3-hexenyl, 5,6-dihydroxy-5-methyl-yl-3-hexenyl, 5-ethyl-5-hydroxy-3-heptynyl, 5-ethyl-6-hydroxy-3-heptynyl, 5-ethyl-5,6-dihydroxy-3-heptynyl, 5-hydroxy-5-(n-propyl)-3-octynyl, 6-hydroxy-5-(n-propyl)-3-octynyl, 5,6-dihydroxy-5-(n-propyl)-3-octynyl, 4-hydroxy-5-methyl-2-hexynyl, 5-hydroxy-5-methyl-2-hexynyl, 6-hydroxy-5-methyl-2-hexynyl, 4,5-dihydroxy-5-ethyl-2-hexynyl, 4,6-dihydroxy-5-methyl-2-hexynyl, 5,6-dihydroxy-5-methyl-2-hexynyl, 5-ethyl-4-hydroxy-2-heptynyl, 5-ethyl-5-hydroxy-2-heptynyl, 5-ethyl-6-hydroxy-2-heptynyl, 5-ethyl-4,5-dihydroxy-2-heptynyl, 5-ethyl-4,6-dihydroxy-2-heptynyl, 5-ethyl-5,6-dihydroxy-2-heptynyl, 4-hydroxy-5-(n-propyl)-2-octynyl, 5-hydroxy-5-(n-propyl)-2-octynyl, 6-hydroxy-5-(n-propyl)-2-octynyl, 4,5-dihydroxy-5-(n-propyl)-2-octynyl, 4,6-dihydroxy-5-(n-propyl)-2-octynyl, 5,6-dihydroxy-5-(n-propyl)-2-octynyl, 4-hydroxy-5-methyl-1-hexynyl, 5-hydroxy-5-methyl-1-hexynyl, 6-hydroxy-5-methyl-1-hexynyl, 4,5-dihydroxy-5-methyl-1-hexynyl, 4,6-dihydroxy-5-methyl-1-hexynyl, 5,6-dihydroxy-5-methyl-1-hexynyl, 5-ethyl-4-hydroxy-1-heptynyl, 5-ethyl-5-hydroxy-1-heptynyl, 5-ethyl-6-hydroxy-1-heptynyl, 5-ethyl-4,5-dihydroxy-1-heptynyl, 5-ethyl-4,6-dihydroxy-1-heptynyl, 5-ethyl-5,6-dihydroxy-1-heptynyl, 4-hydroxy-5-(n-propyl)-1-octynyl, 5-hydroxy-5-(n-propyl)-1-octynyl, 6-hydroxy-5-(n-propyl)-1-octynyl, 4,5-dihydroxy-5-(n-propyl)-1-octynyl, 4,6-dihydroxy-5-(n-propyl)-1-octynyl and 5,6-dihydroxy-5-(n-propyl)-1-octynyl groups.

Preferable examples thereof include 2-methyl-propyl, 1-cyclopropyl-1-hydroxymethyl, 1-hydroxy-2-methylpropyl, 2-hydroxy-2-methylpropyl, 3-hydroxy-2-methylpropyl, 2,3-dihydroxy-2-methylpropyl, 2-ethyl-2-hydroxybutyl, 2-ethyl-3-hydroxybutyl, 2-ethyl-2,3-dihydroxybutyl, 3-hydroxy-3-methylbutyl, 4-hydroxy-3-methylbutyl, 3,4-dihydroxy-3-methylbutyl, 3-ethyl-3-hydroxypentyl, 3-ethyl-4-hydroxypentyl, 3-ethyl-3,4-dihydroxypentyl, 3-hydroxy-3-methyl-1-butenyl, 4-hydroxy-3-methyl-1-butenyl, 3,4-dihydroxy-3-methyl-1-butenyl, 3-ethyl-3-hydroxy-1-pentenyl, 3-ethyl-4-hydroxy-1-pentenyl, 3-ethyl-3,4-dihydroxy-1-pentenyl, 3-hydroxy-3-methyl-1-butynyl, 4-hydroxy-3-methyl-1-butynyl, 3,4-dihydroxy-3-methyl-1-butynyl, 3-ethyl-3-hydroxy-1-pentynyl, 3-ethyl-4-hydroxy-1-pentynyl and 3-ethyl-3,4-dihydroxy-1-pentynyl groups.

In each of the general formulae 1 to 3, $R^3$ is preferably a hydroxyl group, and both $R^1$ and $R^3$ are preferably hydroxyl groups. In this case, $R^2$ is preferably a hydrogen atom or hydroxypropoxyl group. When $R^3$ is a hydroxyl group, X is preferably —O—CH$_2$—, —CH$_2$—CH$_2$— or —CH=CH—.

When both $R^1$ and $R^3$ are hydroxyl groups, $R^2$ is a hydrogen atom, and X is the above-described preferable group, R is preferably —CH$_2$—C(CH$_3$)$_2$OH or —CH$_2$—CH(CH$_3$)$_2$.

The provitamin D derivative represented by the general formula 1 is dissolved in a proper solvent to provide a solution, and the solution of the provitamin D derivative is irradiated with the ultraviolet rays having the specific wavelength from the ultraviolet irradiation apparatus as mentioned above to conduct a photochemical reaction, thereby forming the previtamin D derivative represented by the general formula 2.

Examples of the reaction solvent include ether solvents such as tetrahydrofuran, diethyl ether, diisopropyl ether and dioxane, alcohol solvents such as methanol, ethanol, propanol and isopropanol, hydrocarbon solvents such as pentane, hexane, heptane, cyclohexane, benzene, toluene and xylene, and halogenated hydrocarbon solvents such as dichloromethane, 1,2-dichloroethane, chlorobenzene, bromobenzene, chloroform and carbon tetrachloride.

The amount of the reaction solvent used is generally 10 to 100,000 times, preferably 20 to 1,000 times as much as the used provitamin D derivative represented by the general formula 1. The reaction temperature is within a range of generally from about −50° C. to about 50° C., preferably from about −10° C. to about 15° C. The reaction time is generally about 1 to 1,000 minutes, preferably about 10 to 100 minutes per gram of the provitamin D derivative represented by the general formula 1.

The isolation and purification of the previtamin D derivative represented by the general formula 2 from the reaction mixture obtained in such a manner are conducted in accordance with the same method as that used in the ordinary isolation and purification of organic compounds. For example, the reaction mixture is concentrated under reduced pressure, and the resultant residue is then purified by recrystallization, chromatography or the like.

As the chromatography, either normal phase system or reversed phase system may be used. Examples of the isolation solvent in the normal phase system include ethyl acetate/hexane and methylene chloride/ethanol systems. However, the solvent is not limited to these systems. Examples of the isolation solvent in the reversed phase system include acetonitrile/water and methanol/acetonitrile/water systems. However, the solvent is not limited to these systems. In order to efficiently isolate the intended substance, the kinds of the isolation solvent and a packing material used, and a load against a column must be suitably selected.

In case that the vitamin D derivative represented by the general formula 3 is finally to be derived from the previtamin D derivative represented by the general formula 2, the isolation and purification of the previtamin D derivative are not always required, but the reaction mixture containing the previtamin D derivative represented by the general formula 2 can also be subjected to the next reaction as it is.

The conversion of the previtamin D derivative represented by the general formula 2 into the vitamin D derivative represented by the general formula 3 is conducted by subjecting to a thermal isomerization reaction.

Examples of the reaction solvent in this thermal isomerization reaction include ether solvents such as tetrahydrofuran, diethyl ether, diisopropyl ether and dioxane, alcohol solvents such as methanol, ethanol, propanol and isopropanol, ester solvents such as methyl acetate, ethyl acetate and methyl propionate, ketone solvents such as acetone and methyl ethyl ketone, hydrocarbon solvents such as pentane, hexane, heptane, cyclohexane, benzene, toluene and xylene, and halogenated hydrocarbon solvents such as dichloromethane, 1,2-dichloroethane, chlorobenzene, bromobenzene, chloroform and carbon tetrachloride.

The amount of the reaction solvent used is generally 1 to 1,000 times, preferably 5 to 20 times, more preferably 10 times as much as 1 gram of the previtamin D derivative represented by the general formula 2.

The reaction temperature is within a range of generally from about −20° C. to 120° C., preferably from about 0° C. to 100° C., more preferably from about 20° C. to 30° C. The reaction time is generally about 10 minutes to 6 days, or about 3 to 6 days when the reaction temperature is about 20 to 30° C. As described in literature, the reaction temperature and reaction time may be suitably selected (Journal of Pharmaceutical Sciences, Vol. 57, p. 1326 (1968)).

The isolation and purification of the vitamin D derivative represented by the general formula 3 from the reaction mixture obtained in such a manner are conducted in accordance with the same method as that used in the ordinary isolation and purification of organic compounds. For example, the reaction mixture is concentrated under reduced pressure, and the resultant residue is then purified by recrystallization, chromatography or the like.

As the chromatography, either normal phase system or reversed phase system may be used. Examples of the isolation solvent in the normal phase system include ethyl acetate/hexane and methylene chloride/ethanol systems. However, the solvent is not limited to these systems. Examples of the isolation solvent in the reversed phase system include acetonitrile/water and methanol/acetonitrile/water systems. However, the solvent is not limited to these systems. In order to efficiently isolate the intended substance, the kinds of the isolation solvent and a packing material used, and a load against a column must be suitably selected.

With respect to an oily compound obtained by purification by the chromatography, the intended substance may be provided as crystals by its crystallization. Examples of a solvent used in the crystallization include single solvent such as acetone, diethyl ether, diisopropyl ether, acetonitrile, methyl formate, ethyl acetate, methyl acetate, pentane, hexane and heptane, and mixed solvents such as ethyl acetate/hexane, ethyl acetate/heptane and ethanol/water.

EXAMPLES

The present invention will hereinafter be described by the following Examples. However, the present invention is not limited to these examples.

Example 1

As an ultraviolet irradiation apparatus for photochemical reactions, was used that having an electric discharge lamp 11 composed of a xenon-mercury lamp of rated power of 5 kW, an interference filter 16 the selected transmission wavelength of which is 280 to 320 nm, and a quartz rod 20 in the form of a rectangular pole as illustrated in FIG. 3(A) according to the construction illustrated in FIG. 4.

In 1 liter of tetrahydrofuran, were dissolved 42 g (content: 89.1%) of (1S,3R,20S)-20-(3-hydroxy-3-methylbutoxy) pregna-5,7-diene-1,3-diol, and the resultant solution was stirred at a temperature of −3 to 1° C. by a magnetic stirrer while introducing argon gas. A cell container was continuously irradiated for 1512 minutes with ultraviolet rays having a specific wavelength from the ultraviolet irradiation apparatus while circulating the solution in a proportion that the flow rate of the photo-reactive solution in the cell container amounts to 0.2 liters/min. In this apparatus, the capacity of the cell container is 3 milliliters, and the interior thickness thereof is 0.5 mm.

With respect to a solution obtained by the above photochemical reaction, the content of (6Z)-(1S,3R,20S)-20-(3-hydroxy-3-methylbutoxy)-9,10-secopregna-5(10),6,8-triene-1,3-diol that is a previtamin D derivative of the intended product was determined by high performance liquid chromatography (HPLC) and was found to be 22.5 g (yield: 60.1%).

The reaction mixture thus obtained was purified by means of an industrial preparative HPLC (high performance liquid chromatograph) making use of a mixed solvent of ethyl acetate/n-hexane (weight ratio=85/15) as a developing solvent, thereby obtaining 26.8 g of (6Z)-(1S,3R,20S)-20-(3-hydroxy-3-methylbutoxy)-9,10-secopregna-5(10),6,8-triene-1,3-diol.

This product was dissolved in 0.286 liters of tetrahydrofuran to conduct an isomerization reaction at 24 to 28° C. for 4 to 5 days. The reaction mixture thus obtained was purified by means of the industrial preparative HPLC making use of the same mixed solvent as that used above to obtain 12.7 g of oily substance of (+)(5Z,7E)-(1S,3R,20S)-20-(3-hydroxy-3-methylbutoxy)-9,10-secopregna-5,7,10(19)-triene-1,3-diol. This product was crystallized by using a mixed solvent of ethyl acetate and n-hexane to obtain 9.83 g of crystals of (+)(5Z,7E)-(1S,3R,20S)-20-(3-hydroxy-3-methylbutoxy)-9,10-secopregna-5,7,10(19)-triene-1,3-diol. The yield was 26.3%.

The results of identification of this substance were as follows:
Infrared absorption spectrum (wave number $cm^{-1}$): 3400, 1637, 1056, 895; ultraviolet absorption spectrum ($\lambda_{max}$): 265 nm, purity (RP-HPLC): 99.9%, melting point: 102.6 to 105.5° C.

Example 2

The ultraviolet irradiation apparatus for photochemical reactions illustrated in FIG. 1 was used to irradiate a solution obtained by dissolving 5.0 g (content: 94.3%) of (1S,3R,20S)-20-(3-hydroxy-3-methylbutoxy)pregna-5,7-diene-1,3-diol in 5 liters of tetrahydrofuran continuously for 150 minutes with ultraviolet rays having a specific wavelength from the ultraviolet irradiation apparatus while stirring the solution at a temperature of −9 to −7° C. by a stirrer with introduction of argon gas.

With respect to a solution obtained as a result of the above photochemical reaction, the content of (6Z)-(1S,3R,20S)-20-(3-hydroxy-3-methylbutoxy)-9,10-secopregna-5(10),6,8-triene-1,3-diol that is the intended product was determined by high performance liquid chromatography (HPLC) and was found to be 2.84 g (yield: 60.3%).

Example 3

The ultraviolet irradiation apparatus for photochemical reactions illustrated in FIG. 1 was used to irradiate a solution obtained by dissolving 20 g of (1S,3R,20S)-cholesta-5,7-diene-1,3-diol in 5 liters of tetrahydrofuran continuously for 480 minutes with ultraviolet rays having a specific wavelength from the ultraviolet irradiation apparatus while stirring the solution at a temperature of −4 to −2° C. by a stirrer with introduction of argon gas.

With respect to a solution obtained as a result of the above photochemical reaction, the yield of (6Z)-(1S,3R,20S)-9,10-secocholesta-5(10),6,8-triene-1,3-diol that is the intended product was determined by high performance liquid chromatography (HPLC) and was found to be 66.4%.

Example 4

The ultraviolet irradiation apparatus for photochemical reactions illustrated in FIG. 5 was used. A solution obtained by dissolving 3 mg of (1S,2R,3R,20S)-2-(3-hydroxypropoxy)cholesta-5,7-diene-1,3,25-triol in 3 milliliters of tetrahydrofuran was placed in the small-sized cell container to continuously irradiate the small-sized cell container for 120 seconds with ultraviolet rays having a specific wavelength from the ultraviolet irradiation apparatus at room temperature while stirring the solution by a magnetic stirrer.

With respect to a solution obtained as a result of the above photochemical reaction, the yield of (6Z)-(1S,2R,3R,20S)-2-(3-hydroxypropoxy)-9,10-secocholesta-5(10),6,8-triene-1,3,25-triol that is the intended product was determined by high performance liquid chromatography (HPLC) and was found to be 50.3%.

Example 5

The ultraviolet irradiation apparatus for photochemical reactions illustrated in FIG. 5 was used. A solution obtained by dissolving 3 mg of provitamin $D_2$ (ergosterol) in 3 milliliters of tetrahydrofuran was placed in the small-sized cell container to continuously irradiate the small-sized cell container for 140 seconds with ultraviolet rays having a specific wavelength from the ultraviolet irradiation apparatus at room temperature while stirring the solution by a magnetic stirrer.

With respect to a solution obtained as a result of the above photochemical reaction, the yield of previtamin $D_2$ that is the intended product was determined by high performance liquid chromatography (HPLC) and was found to be 53.7%.

Example 6

The ultraviolet irradiation apparatus for photochemical reactions illustrated in FIG. 5 was used. A solution obtained by dissolving. 3 mg of provitamin $D_3$ (7-dehydrocholesterol) in 3 milliliters of tetrahydrofuran was placed in the small-sized cell container to continuously irradiate the small-sized cell container for 160 seconds with ultraviolet rays having a specific wavelength from the ultraviolet irradiation apparatus at room temperature while stirring the solution by a magnetic stirrer.

With respect to a solution obtained as a result of the above photochemical reaction, the yield of previtamin $D_3$ that is the intended product was determined by high performance liquid chromatography (HPLC) and was found to be 61.1%.

In Example 1 described above used was the photo-reactive solution at a high concentration in the apparatus illustrated in FIG. 4, while in Example 2 used was the photo-reactive solution at a low concentration in the apparatus illustrated in FIG. 1, it has been confirmed that in both examples, an efficiency as greatly high as at least 60% in terms of the yield is achieved. It is apparent that the numerical values of the yield are extremely superior in view of the fact that the yield of the intended vitamin D derivative is several percent to ten-odd percent in the case of the conventional processes.

The reason why such a far excellent efficiency of the photochemical reaction is achieved is considered to be attributable to the fact that according to the ultraviolet irradiation apparatus for photochemical reactions of the present invention, the ultraviolet rays having the specific wavelength of 280 to 320 nm obtained by means of the interference filter are transmitted by the quartz rod in a state that a loss is scarcely caused, to be struck on the photo-reactive solution.

Although the description has been given above on the cases where the ultraviolet irradiation apparatus for photochemical reactions according to the present invention were used to conduct the syntheses of previtamin D derivatives, the intended photochemical reactions, to which the ultraviolet irradiation apparatus according to the present invention are applied, are not limited to the synthetic reactions of previtamin D derivatives, but the apparatus can be applied to various photochemical reactions of photo-reactive solutions, which can be induced by ultraviolet radiation. Therefore, they can be widely used as ultraviolet irradiation apparatus for, for example, syntheses of 6-nylon and benzene hexachloride, and other photochemical reactions intended for organic compound solutions.

EFFECTS OF THE INVENTION

According to the ultraviolet irradiation apparatus of the present invention, ultraviolet rays having a specific wavelength selected by the optical filter can be struck on a photo-reactive solution at a high efficiency by utilizing the quartz rod, so that the intended photochemical reaction of the photo-reactive solution, such as a synthetic reaction of a compound by photochemical reaction, can be caused at a very high efficiency.

The ultraviolet irradiation apparatus according to the present invention can be extremely preferably used in, particularly, synthetic reactions of previtamin D derivatives that are intermediates for syntheses of vitamin D derivatives.

According to the preparation process of a vitamin D derivative of the present invention, a provitamin D derivative can be converted into a previtamin D derivative at a high efficiency by a photochemical reaction by one-step process of light irradiation by using the specific ultraviolet irradiation apparatus for photochemical reactions, by which ultraviolet rays having a specific wavelength obtained by the optical system having wavelength selective property are emitted through the quartz rod. Therefore, a vitamin D derivative can be prepared at a high efficiency by subjecting the previtamin D derivative to a thermal isomerization reaction.

What is claimed is:

1. A process for preparing a vitamin D derivative, comprising:

providing a reaction container configured to contain a solution of a provitamin D derivative and an ultraviolet irradiation apparatus configured to irradiate the solution of the provitamin D derivative in the reaction container with an ultraviolet irradiation, the ultraviolet irradiation apparatus comprising an ultraviolet radiation-emitting lamp, an optical system positioned to be struck by light from the ultraviolet radiation-emitting lamp and configure to emit ultraviolet rays having a specific wavelength, a quartz rod positioned to be struck by the ultraviolet rays from the optical system, and a projection lens positioned to be struck by and to irradiate the solution of the provitamin D derivative in the reaction container with the ultraviolet rays through the quartz rod, the projection lens being configured to control a spot size of the ultraviolet rays having the specific wavelength;

irradiating the solution of the provitamin D derivative with the ultraviolet rays emitted from the projection lens of the ultraviolet irradiation apparatus to cause a photochemical reaction of the provitamin D derivative and form a previtaniin D derivative; and subjecting the previtamin D derivative to a thermal isomerization reaction to prepare the vitamin D derivative.

2. The process according to claim 1, wherein the provitamin D derivative is a compound represented by the following general formula 1, the previtamin D derivative is a compound represented by the following general formula 2, and the vitamin D derivative is a compound represented by the following general formula 3, General Formula 1

General Formula 2

General Formula 3 wherein $R^1$ and $R^3$ individually is a hydrogen atom or a hydroxyl group which may have a protecting group, $R^2$ is a hydrogen atom, a hydroxyl group which has a protecting group, a lower alkoxy group having 1 to 10 carbon atoms which may be substituted or a lower alkyl group having 1 to 10 carbon atoms which may be substituted, R is a hydrogen atom or a lower alkyl group having 1 to 10 carbon atoms which maybe substituted, and X represents —O—CH$_2$—, —S—CH$_2$—, —CH$_2$—CH$_2$—, —CH=CH— or —N—(R$^4$)—CH$_2$—, in which $R^4$ is a hydrogen atom or a lower alkyl group having 1 to 10 carbon atoms which may be substituted.

3. The preparation process according to claim 1, wherein the irradiation comprises irradiating a solution of the provitamin D derivative represented by the general formula 1 with the ultraviolet rays to cause a photochemical reaction of the provitamin D derivative solution, thereby forming the previtamin D derivative represented by the general formula 2.

4. The preparation process according to claim 3, wherein in the general formulae 1 and 2, $R^3$ is a hydroxyl group, and X is —O—CH$_2$—.

5. The preparation process according to claim 4, wherein in the general formulae 1 and 2, $R^1$ is a hydroxyl group.

6. The preparation process according to claim 5, wherein in the general formulae 1 and 2, $R^2$ is a hydrogen atom.

7. The preparation process according to claim 6, wherein in the general formulae 1 and 2, R is —CH$_2$—C(CH$_3$)$_2$OH.

8. The preparation process according to claim 6, wherein in the general formulae 1 and 2, R is —CH$_2$—CH(CH$_3$)$_2$.

9. The preparation process according to claim 3, wherein in the general formulae 1 and 2, $R^3$ is a hydroxyl group, and X is —CH$_2$—CH$_2$—.

10. The preparation process according to claim 9, wherein in the general formulae 1 and 2, $R^1$ is a hydroxyl group.

11. The preparation process according to claim 10, wherein in the general formulae 1 and 2, $R^2$ is a hydrogen atom.

12. The preparation process according to claim 11, wherein in the general formulae 1 and 2, R is —CH$_2$—C(CH$_3$)$_2$OH.

13. The preparation process according to claim 11, wherein in the general formulae 1 and 2, R is —CH$_2$—CH(CH$_3$)$_2$.

14. The preparation process according to claim 10, wherein in the general formulae 1 and 2, $R^2$ is a hydroxypropoxy group.

15. The preparation process according to claim 14, wherein in the general formulae 1 and 2, R is —CH$_2$—C(CH$_3$)$_2$OH.

16. The preparation process according to claim 14, wherein in the general formulae 1 and 2, R is —CH$_2$—CH(CH$_3$)$_2$.

17. The preparation process according to claim 3, wherein in the general formulae 1 and 2, $R^3$ is a hydroxyl group, and X is —CH=CH—.

18. The preparation process according to claim 17, wherein in the general formulae 1 and 2, $R^1$ is a hydroxyl group.

19. The preparation process according to claim 18, wherein in the general formulae 1 and 2, $R^2$ is a hydrogen atom.

20. The preparation process according to claim 19, wherein in the general formulae 1 and 2, R is —CH$_2$—C(CH$_3$)$_2$OH.

21. The preparation process according to claim 19, wherein in the general formulae 1 and 2, R is —CH$_2$—CH(CH$_3$)$_2$.

22. The preparation process according to claim 2, wherein in the general formulae 1, 2 and 3, $R^3$ is a hydroxyl group, and X is —O—CH$_2$—.

23. The preparation process according to claim 22, wherein in the general formulae 1, 2 and 3, $R^1$ is a hydroxyl group.

24. The preparation process according to claim 23, wherein in the general formulae 1, 2 and 3, $R^2$ is a hydrogen atom.

25. The preparation process according to claim 24, wherein in the general formulae 1, 2 and 3, R is —CH$_2$—C(CH$_3$)$_2$OH.

26. The preparation process according to claim 24, wherein in the general formulae 1, 2 and 3, R is —CH$_2$—CH(CH$_3$)$_2$.

27. The preparation process according to claim 2, wherein in the general formulae 1, 2 and 3, R$^3$ is a hydroxyl group, and X is —CH$_2$CH$_2$—.

28. The preparation process according to claim 27, wherein in the general formulae 1, 2 and 3, R$^1$ is a hydroxyl group.

29. The preparation process according to claim 28, wherein in the general formulae 1, 2 and 3, R$^2$ is a hydrogen atom.

30. The preparation process according to claim 29, wherein in the general formulae 1, 2 and 3, R is —CH$_2$—C(CH$_3$)$_2$OH.

31. The preparation process according to claim 29, wherein in the general formulae 1, 2 and 3, R is —CH$_2$—CH(CH$_3$)$_2$.

32. The preparation process according to claim 28, wherein in the general formulae 1, 2 and 3, R$^2$ is a hydroxypropoxy group.

33. The preparation process according to claim 32, wherein in the general formulae 1, 2 and 3, R is —CH$_2$—C(CH$_3$)$_2$OH.

34. The preparation process according to claim 32, wherein in the general formulae 1, 2 and 3, R is —CH$_2$CH(CH$_3$)$_2$.

35. The preparation process according to claim 2, wherein in the general formulae 1, 2 and 3, R$^3$ is a hydroxyl group, and X is —CH=CH—.

36. The preparation process according to claim 35, wherein in the general formulae 1, 2 and 3, R$^1$ is a hydroxyl group.

37. The preparation process according to claim 36, wherein in the general formulae 1, 2 and 3, R$^2$ is a hydrogen atom.

38. The preparation process according to claim 37, wherein in the general formulae 1, 2 and 3, R is —CH$_2$—C(CH$_3$)$_2$OH.

39. The preparation process according to claim 37, wherein in the general formulae 1, 2 and 3, R is —CH$_2$—CH(CH$_3$)$_2$.

40. The preparation process according to claim 1, wherein the projection lens is configured to control a diameter of the spot size.

41. The preparation process according to claim 1, wherein the projection lens is configured to control a density of the ultraviolet rays having the specific wavelength.

42. A process for preparing a vitamin D derivative, comprising:
    providing a reaction container configured to contain a solution of a provitamin D derivative and an ultraviolet irradiation apparatus configured to irradiate the solution of the provitamin D derivative in the reaction container with an ultraviolet irradiation, the ultraviolet irradiation apparatus comprising an ultraviolet radiation-emitting lamp, an optical system positioned to be struck by light from the ultraviolet radiation-emitting lamp and configured to emit ultraviolet rays having a specific wavelength, and a quartz rod positioned to be struck by the ultraviolet rays from the optical system and configured to directly irradiate the solution of the provitamin D derivative in the reaction container with the ultraviolet rays;
    irradiating the solution of the provitamin D derivative in the reaction container with the ultraviolet rays emitted from the quartz rod of the ultraviolet irradiation apparatus to cause a photochemical reaction of the provitamin D derivative and form a previtamin D derivative; and
    subjecting the previtamin D derivative to a thermal isomerization reaction to prepare the vitamin D derivative.

43. The preparation process according to claim 42, wherein the quartz rod is configured to be immersed into the solution of the provitamin D derivative in the reaction container.

* * * * *